US007108988B2

(12) United States Patent
Sherman et al.

(10) Patent No.: US 7,108,988 B2
(45) Date of Patent: Sep. 19, 2006

(54) METHODS OF IDENTIFYING AGENTS FOR INHIBITING LENTIVIRUS REPLICATION

(75) Inventors: Michael Sherman, San Francisco, CA (US); Warner Greene, San Francisco, CA (US); Ulrich Schubert, Hamburg (DE); Victor Wray, Braunschweig (DE); Uwe Tessmer, Hamburg (DE); Peter Henklein, Berlin (DE); Karsten Bruns, Hamburg (DE)

(73) Assignee: The J. David Gladstone Institutes, San Francisco, CA (US)

( * ) Notice: Subject to any disclaimer, the term of this patent is extended or adjusted under 35 U.S.C. 154(b) by 518 days.

(21) Appl. No.: 10/285,263

(22) Filed: Oct. 30, 2002
(Under 37 CFR 1.47)

(65) Prior Publication Data
US 2004/0009909 A1  Jan. 15, 2004

Related U.S. Application Data

(60) Provisional application No. 60/350,168, filed on Nov. 2, 2001.

(51) Int. Cl.
*C12Q 1/70* (2006.01)

(52) U.S. Cl. .................. 435/7.1; 435/5; 435/69.7; 436/501

(58) Field of Classification Search ............ 435/51, 435/7.1, 69.7; 536/50
See application file for complete search history.

(56) References Cited

U.S. PATENT DOCUMENTS

| 4,814,323 | A | 3/1989 | Andrieu et al. |
| 5,604,092 | A | 2/1997 | Erlanger et al. |
| 5,612,018 | A | 3/1997 | Bonyhadi et al. |
| 5,639,598 | A | 6/1997 | Weiner et al. |
| 5,767,069 | A | 6/1998 | Ko et al. |
| 5,773,225 | A | 6/1998 | Luban et al. |
| 5,801,144 | A | 9/1998 | Karpas et al. |
| 5,840,305 | A | 11/1998 | Bukrinsky et al. |
| 5,948,884 | A | 9/1999 | Luchinger |
| 5,976,786 | A | 11/1999 | Finkel et al. |
| 6,030,825 | A | 2/2000 | Hillman et al. |
| 6,177,253 | B1 | 1/2001 | Erlanger et al. |
| 6,270,957 | B1 | 8/2001 | Rich et al. |

FOREIGN PATENT DOCUMENTS

| AU | 6700196 | 2/1997 |
| CA | 2226880 | 2/1997 |
| CN | 1192750 | 9/1998 |
| CZ | 9800051 | 4/1998 |
| EP | 0842191 | 11/2001 |
| JP | 2000502320 | 2/2000 |
| NZ | 315324 | 10/1999 |
| WO | WO 96/25175 | 8/1996 |
| WO | WO 97/04005 | 2/1997 |
| WO | WO 97/33604 | 9/1997 |
| WO | WO 99/10373 | 8/1998 |
| WO | WO 00/15208 | 3/2000 |

OTHER PUBLICATIONS

Muthumani et al. Vpr-GFP virion particle identifies HIV-infected targets and preserves HIV-1 Vpr function in macrophages and T-cells. DNA and Cell Biology (2000) vol. 19, No. 3, pp. 179-188.*

Stauber et al. Direct visualization of HIV-1 entry: Mechanism and role of cell surface receptors. Biochemical Biophysical Research Communications (1999) vol. 258, pp. 695-702.*

Wu et al. Targeting foreign proteins to human immunodeficiency virus particles via fusion with Vpr and Vpx. Journal of Virology (1995) vol. 69, pp. 3389-3398.*

Saphire et al. Trans-complementation rescue of cyclophilin A deficient viruses reveals that the recruitment for cyclophilin A in human immunodeficiency virus type 1 replication is independent of isomerase activity. Journal of Virology (Mar. 2002) vol. 76.*

Sherman, et al., Nucleocytoplasmic Shuttling by Human Immunodeficiency Virus Type 1 Vpr. , Journal of Virology, Feb. 2001, vol. 75, No. 3, pp. 1522-1532.

Liu et al., Peptidyl-prolyl cis-trans-isomerase from *Escheria coli*: Periplasmic Homolog of Cyclophilin that is not inhibited by Cyclosporine A. Proceedings of the National Academy of Science, Jun. 1990, vol. 87, No. 11, pp. 4028-4032.

Zhao, et al.Cyclophilin A Complexed with a Fragment of HIV-1 Gag Protein: Insights into HIV-1 Infectious Activity. Structure. Jan. 1997, vol. 5, No. 1, pp. 139-146.

Braaten, et al. "Cyclophilin A regulates HIV-1 infectivity, as demonstrated by gene targeting in human T cells", *The EMBO Journal* (2001) vol. 20(6): 1300-1309.

Carpentier, et al. "Delineation of the calcineurin-interacting region of cyclophilin B", *Protein Science* , (2000) vol. 9: 2836-2393.

Cohen, et al. "Human immunodeficiency virus *vpr* product is a virion-associated regulatory protein", *J. Virology*, (1990) vol. 64(6): 3097-3099.

(Continued)

*Primary Examiner*—Ulrike Winkler
(74) *Attorney, Agent, or Firm*—Paula A. Borden; Bozicevic, Field & Francis, LLP

(57) ABSTRACT

The present invention provides screening methods for identifying a compound that induces loss of the lentiviral protein Vpr; screening methods for identifying compounds that inhibit the peptidyl-prolyl cis/trans isomerase (PPIase) activity of a protein that catalyzes cis-trans isomerization of cis-peptidylprolyl bonds in Vpr; and compounds identified by the screening methods. The compounds are useful for treating a lentiviral infection. The present invention further provides methods of inducing loss of the lentiviral protein Vpr; methods of inhibiting lentivirus viral replication; and methods of treating a lentivirus infection in an individual. The methods generally involve administering to an individual infected with the lentivirus an effective amount of a compound that induces Vpr loss and/or that inhibits PPIase activity of a protein that catalyzes cis-trans isomerization of cis-peptidylprolyl bonds in Vpr.

9 Claims, 7 Drawing Sheets

OTHER PUBLICATIONS

He, et al. "Human immunodeficiency virus type 1 viral protein R (vpr) arrests cells in the $G_2$ phase of the cell cycle by inhibiting $p34^{cdc2}$ activity", *J. Virology*, (1995) vol. 69(11): 6705-6711.

Heinsinger, et al. "The vpr protein of human immunodeficiency virus type 1 influences nuclear localization of viral nucleic acids in nondividing host cells", *Proc. Natl. Acad. Sci. USA*, (1994) vol. 91; 7311-7315.

Kondo, et al. "A conserved LXXLF sequence is the major determinant in p6$^{gag}$ required for the incorporation of human immunodeficiency virus type 1 vpr", *J. Virology*, (1996) vol. 70(1): 159-164.

Mlynar, et al. "The non-immunosuppressive cyclosporin A analogue SDZ NIM 811 inhibits cyclophilin A incorporation into virions and virus replication in human immunodeficiency virus type 1-infected primary and growth-arrested T cells", *J. General Virology*, (1997) vol. 78: 825-835.

Rizzardi, et al. "Treatment of primary HIV-1 infection with cyclosporin A coupled with highly active antiretroviral therapy", *J. Clin. Investigation*, (2002) vol. 109(5): 681-688.

* cited by examiner

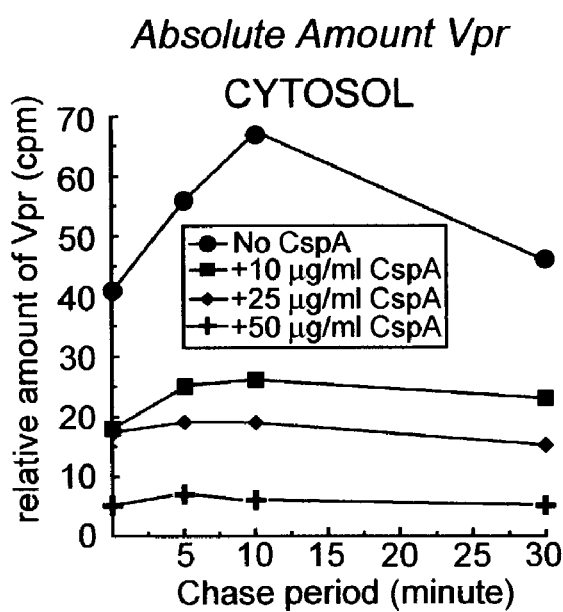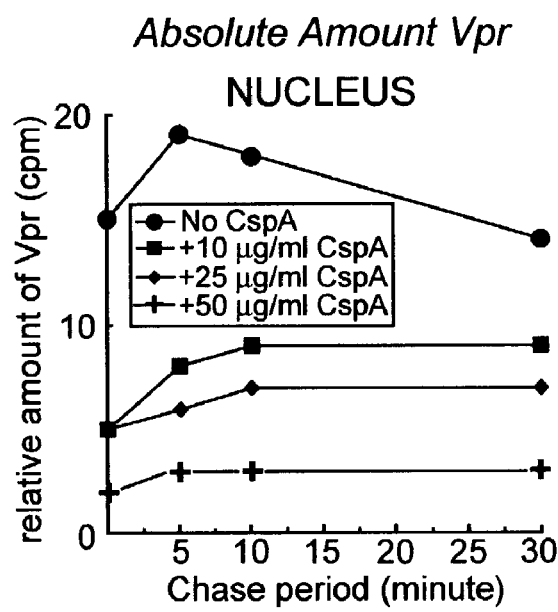
FIG. 3A
FIG. 3B

Sequence alignment Vpr-CA and localization of potential CyPA binding site and conserved Pro residues.

METHODS OF IDENTIFYING AGENTS FOR INHIBITING LENTIVIRUS REPLICATION

CROSS-REFERENCE

This application claims the benefit of U.S. Provisional Patent Application No. 60/350,168, filed Nov. 2, 2001, which application is incorporated herein by reference in its entirety.

FIELD OF THE INVENTION

This invention is in the field of treating lentivirus infections.

BACKGROUND OF THE INVENTION

Human immunodeficiency virus (HIV) is the etiologic agent of acquired immunodeficiency syndrome (AIDS). HIV infection leads to depletion of CD4$^+$ T lymphocytes. AIDS is characterized by various pathological conditions, including immune incompetence, opportunistic infections, neurological dysfunctions, and neoplastic growth.

Several drugs have been approved for treatment of this devastating disease, including azidovudine (AZT), didanosine (dideoxyinosine, ddO), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). However, none of the available drugs used to combat HIV is completely effective, and treatment frequently gives rise to drug-resistant virus. Thus, the search for new anti-HIV drugs continues.

HIV is a member of the lentivirus family of retroviruses. Among the viral proteins is group specific antigen (Gag). Gag associates with the plasma membrane, where viral assembly takes place.

Cyclophilin A (CyPA) is a cellular protein having immunomodulatory activity, is believed to be incorporated into HIV virions by binding to the HIV Gag protein p24$^{CA}$ (p24 capsid protein), and is thought to be required for productive viral infection. The Gag-CyPA complex contained in the core of the virion is surrounded by a lipid envelope bearing HIV envelope glycoproteins. Cyclophilin A (CyPA) is a cis/trans peptidyl prolyl isomerase that has been shown to bind to the immunosuppressive drug cyclosporinA (CsA). Immunosuppression by CsA is thought to result when the cyclophilin-cyclosporin complex binds and inhibits calcinuerin, a calcium-dependent, serine-threonine phosphatase required for transcriptional activation of many cytokine genes in stimulated T cells. The CsA binding site on CyPA is separate and distinct from the portion of CyPA that has peptidyl-prolyl cis/trans isomerase (PPIase) activity and the action of CsA on CyPA does not depend on the PPIase activity. In addition, neither the immunosuppressive activity nor the reported anti-viral activity of CsA depend on the PPIase activity of CyPA.

The therapeutic anti-viral potential of intervention at the level of the CyPA-p24$^{CA}$ interaction has been investigated. However, drug treatments that target the CyPA-p24$^{CA}$ interaction suffer from certain drawbacks, including the following. The treatments are limited to HIV-1 because CyPA is present only in HIV1 but not in HIV-2 virions. The treatments do not effect a complete block of release of virions. The treatment only intervenes at the stage of viral infection, i.e., viral entry into a cell. Once a cell is infected, treatments targeted to inhibiting the CyPA-p24$^{CA}$ interaction are completely ineffective, as such treatments do not reduce viral replication. The CyPA-p24$^{CA}$ interaction does not require the PPIase activity of CyPA; instead, this interaction is limited to the binding of CyPA to Gag.

Another HIV protein, Viral protein R (Vpr; also called "lentiviral R protein" as it is common to all known primate lentiviruses, including HIV-1, HIV-2 and SIV), is a 96-amino acid, 14 kD protein that performs two distinct functions during HIV replication. Vpr is incorporated into the HIV virion and helps to target the viral preintegration complex (PIC) to the nucleus in nondividing cells through its nuclear localization signal. An interaction between Vpr and the p6 portion of the Gag protein is believed to be responsible for the packaging of Vpr into the virion. Vpr is also responsible for arresting HIV infected cells in the G2 phase of the cell cycle, which results in increased virus production. The mechanism of G2 cell cycle arrest is unknown, but Vpr expression has been correlated with a decrease in p34cdc2/cyclin B complex activity.

Despite the availability of a number of drugs to combat HIV infections, there is a need in the art for additional drugs that inhibit HIV replication, and which are suitable for treating HIV and other lentiviral infections.

Literature

Cohen, et al. (1990). *J. Virol.* 64:3097–3099; Bukinsky et al. (1994) *Proc. Natl. Acad. Sci. USA* 91(15):7311–7315; Kondo et al. (1996) *J. Virol.* 70(1):159–64; He et al. (1995) *J. Virol.* 69(11):6705–6711; U.S. Pat. No. 5,612,018; Braaten and Luban (2001) *EMBO J.* 20:1300–1309; U.S. Pat. No. 4,814,323; U.S. Pat. No. 6,270,957; U.S. Pat. No. 5,840,305; U.S. Pat. No. 5,801,144; U.S. Pat. No. 6,030,825; U.S. Pat. No. 5,767,069; Carpentier et al. (1992) *Protein Sci.* 9:2386–2393; WO0015208, U.S. Pat. No. 6,270,957, WO9910373, U.S. Pat. No. 5,840,305, WO9733604, U.S. Pat. No. 5,948,884 WO9704005, EP0842191, JP2000502320, CA2226880, AU6700196, BR9609795 CN1192750, CZ9800051, HU9900405, NO980195, NZ315324, PL324531, U.S. Pat. No. 6,177,253 WO9625175, U.S. Pat. No. 5,773,225, U.S. Pat. No. 5,801,144, U.S. Pat. No. 5,767,069, U.S. Pat. No. 5,604,092; Mlynar et al. (1997) *J Gen Virol* 78:825–35; Rizzardi et al. (2002) *J. Clin. Invest.* 109:681–688.

SUMMARY OF THE INVENTION

The present invention provides screening methods for identifying a compound that induces loss of the lentiviral protein Vpr; screening methods for identifying compounds that inhibit the peptidyl-prolyl cis/trans isomerase (PPIase) activity of a protein that catalyzes cis-trans isomerization of cis-peptidylprolyl bonds in Vpr; and compounds identified by the screening methods. The compounds are useful for treating a lentiviral infection. The present invention further provides methods of inducing loss of the lentiviral protein Vpr; methods of inhibiting lentivirus viral replication; and methods of treating a lentivirus infection in an individual. The methods generally involve administering to an individual infected with the lentivirus an effective amount of a compound that induces Vpr loss and/or that inhibits PPIase activity of a protein that catalyzes cis-trans isomerization of cis-peptidylprolyl bonds in Vpr.

BRIEF DESCRIPTION OF THE DRAWINGS

FIGS. 3A and 3B depict results demonstrating that CsA induces rapid loss of Vpr in the cytosol and the nucleus.

DETAILED DESCRIPTION OF THE INVENTION

Figure 1A:
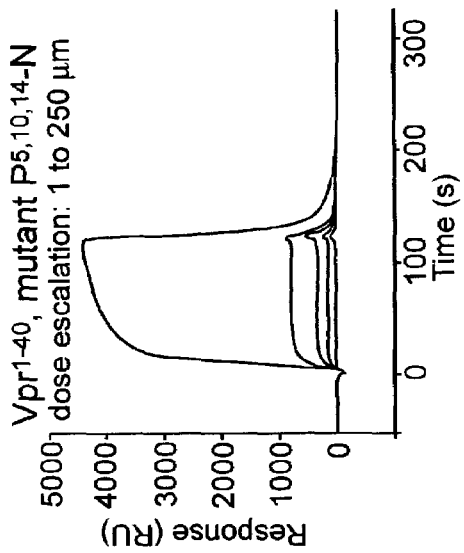
FIGS. 1A–1F depict the results of binding studies on Vpr and CyPA using BIAcore spectroscopy.
Figure 1B:
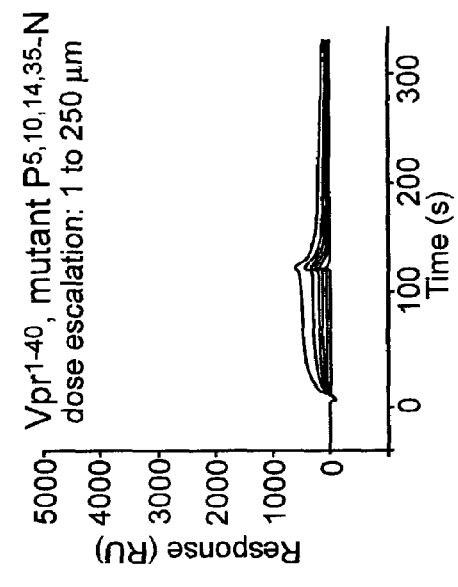
Figure 1C:
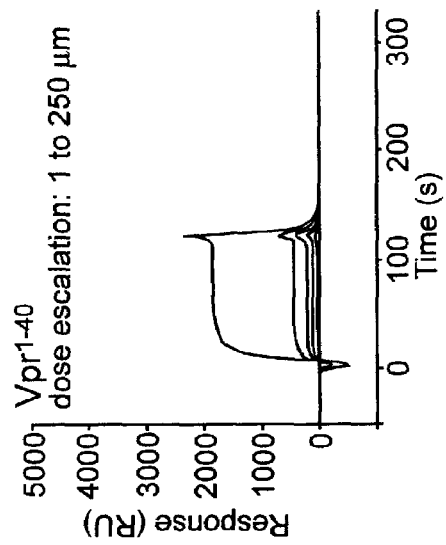
Figure 1D:
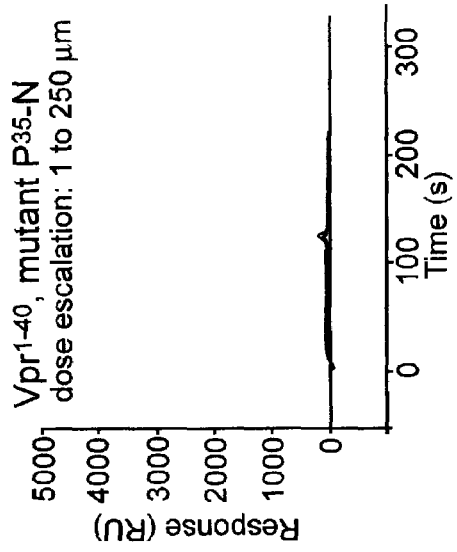
Figure 1F:
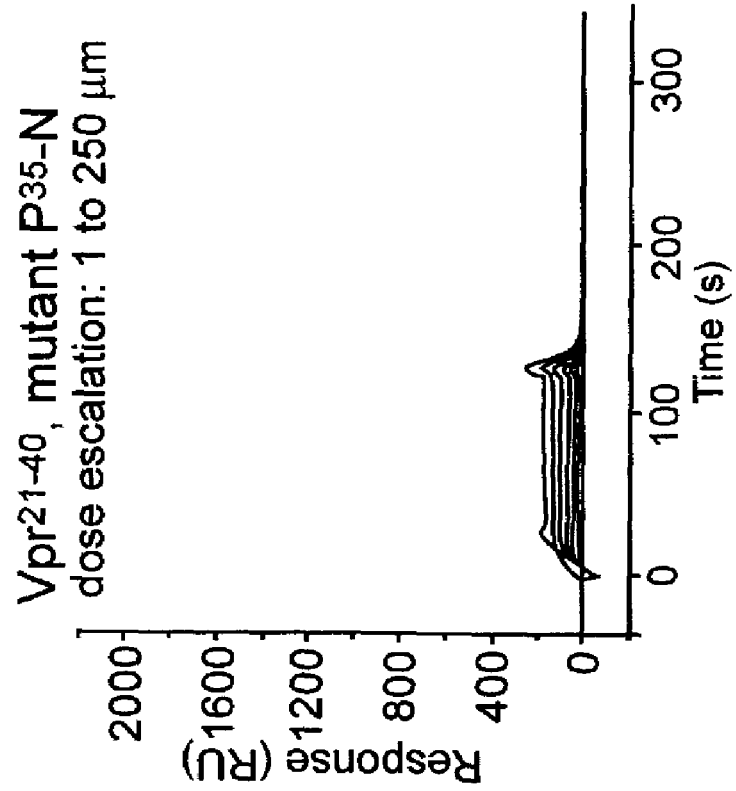
Figure 1E:
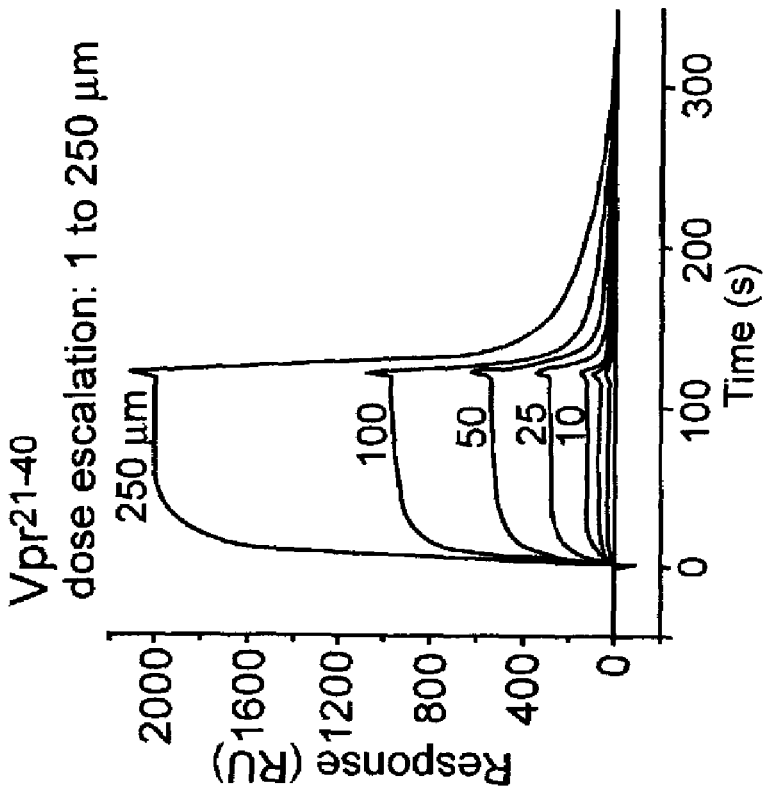

The present invention provides screening methods for identifying a compound that induces loss of lentivirus Vpr in a eukaryotic cell, as well as methods for identifying a compound that inhibits a PPIase activity of a protein that catalyzes cis-trans isomerization of cis-peptidylprolyl bonds in Vpr. Compounds that induce loss of Vpr and/or that inhibit PPIase activity of a protein that catalyzes cis-trans isomerization of cis-peptidylprolyl bonds in Vpr are useful for treating lentiviral infections, including human immunodeficiency virus (HIV) infections. Thus, the invention further provides compounds identified using the screening methods, and compositions, including pharmaceutical compositions, that include the anti-viral compounds.

The invention is based on the observation that cyclosporin A (CsA) induces specific loss of intracellular and virion-associated Vpr when lentivirus-infected cells are contacted with CsA. The observation was made that CyPA affects cotranslational folding of Vpr, and that the PPIase activity of CyPA plays an important role in the level of Vpr in a cell. Reduction of PPIase activity of a protein that catalyzes cis-trans isomerization of cis-peptidylprolyl bonds in Vpr is a target for therapeutic intervention in the treatment of lentivirus infections.

Treatment of HIV-infected individuals with cyclosporin A (CsA) is undesirable, because CsA is immunosuppressive, and HIV-infected individuals are already immunocompromised, due to killing of CD4$^+$ T lymphocytes by the virus and other pathological events related to the HIV infection. Non-immunosuppressive derivatives of CsA are known in the art, and such derivatives have been proposed as therapeutics for treating HIV infection. CsA, non-immunosuppressive derivatives of CsA, SDZ "NIM811," "Sangliphe-rinA" (Novartis), the naturally occurring drugs FK506, and Rapamycin are all believed to act by inhibiting binding of cyclophilin to the HIV-1 Gag protein p24$^{CA}$ (capsid). The observation that cyclosporin induces loss of Vpr indicates that Vpr is a viable target for therapeutic intervention in lentiviral infections.

The present invention further provides methods of inducing specific loss of the lentiviral protein Vpr; methods of inhibiting lentivirus viral replication; and methods of treating a lentivirus infection in an individual. The methods generally involve administering to an individual infected with the lentivirus an effective amount of an agent that induces Vpr loss and/or that inhibits a PPIase activity of a protein that catalyzes cis-trans isomerization of cis-peptidylprolyl bonds in Vpr. Induction of specific loss of Vpr, a protein that is essential to replication of lentiviruses, results in a reduction in lentivirus load.

Features of the Invention

The present invention features a method of inducing Vpr loss in a cell infected with a lentivirus. The method generally involves contacting the cell with an agent that induces Vpr loss. In some embodiments, the agent is a compound that inhibits a peptidyl-prolyl cis/trans isomerase (PPIase) activity of a protein that catalyzes cis-trans isomerization of cis-peptidylprolyl bonds in Vpr in the cell. In some embodiments, the PPIase is a cyclophilin. In some embodiments, the agent induces degradation of Vpr. In many embodiments, the agent is a compound that both inhibits a peptidyl-prolyl cis/trans isomerase activity of a cyclophilin in the cell and that induces degradation of Vpr in the cell. In other embodiments, the agent reduces the level of correct co-translational folding of Vpr in the cell.

The present invention features a method of treating a lentivirus infection in an individual. The method generally involves administering to the individual an effective amount of an agent that induces Vpr loss in a lentivirus-infected cell in the individual, thereby reducing the level of Vpr in the infected cell, wherein a reduction in the level of Vpr in the cell treats a lentivirus infection.

The present invention features a method of reducing lentivirus replication in a cell infected with a lentivirus. The method generally involves contacting the cell with an agent that induces Vpr loss in the cell, thereby reducing the level of Vpr in the cell, wherein a reduction in the level of Vpr in the cell reduces viral replication.

The present invention features a method of reducing lentivirus load in an individual. The method generally involves administering to the individual an effective amount of an agent that induces Vpr loss in a lentivirus-infected cell of the individual, thereby reducing the level of Vpr in the infected cell, wherein a reduction in the level of Vpr in the cell reduces viral load in the individual.

The present invention also features a method of identifying an agent that induces Vpr loss in a lentivirus-infected cell. The method generally involvescontacting a cell that produces Vpr with a test agent; and determining the effect, if any, of the test agent on the level of Vpr in the cell. In some embodiments, the cell produces a Vpr fusion protein, which fusion protein includes Vpr and a fusion partner that provides a detectable signal. In some embodiments, the fusion partner is selected from the group consisting of a fluorescent protein and an immunological tag. In many embodiments, the method further includes determining the effect, if any, of the agent on a peptidyl-prolyl cis/trans isomerase activity of a protein that catalyzes cis-trans isomerization of cis-peptidylprolyl bonds in Vpr, e.g., a cyclophilin.

The invention further features an agent that induces Vpr loss in a lentivirus-infected cell. In many embodiments, the agent is one that inhibits a PPIase activity of a protein that catalyzes cis-trans isomerization of cis-peptidylprolyl bonds in Vpr. In many embodiments, the agent both induces Vpr loss in a lentivirus-infected cell and inhibits a PPIase activity of a protein that catalyzes cis-trans isomerization of cis-peptidylprolyl bonds in Vpr. The agent is one that does not inhibit binding of HIV-Gag to cyclophilinA.

The invention further features a pharmaceutical composition that includes: an agent that induces Vpr loss in a lentivirus-infected cell and/or inhibits a PPIase activity of a cyclophilin; and a pharmaceutically acceptable excipient.

The invention further features a pharmaceutical composition that includes: an agent that induces Vpr loss in a lentivirus-infected cell and/or inhibits a peptidyl-prolyl cis/trans isomerase activity of a protein that catalyzes cis-trans isomerization of cis-peptidylprolyl bonds in Vpr; an anti-HIV agent; and a pharmaceutically acceptable excipient.

Definitions

As used herein, the terms "loss of Vpr" and "specific loss of Vpr" include a reduction in the level of Vpr in a cell infected with a lentivirus, wherein the level of cellular (e.g., non-lentiviral) proteins is unaffected. A loss of Vpr can be a result of a reduction in the level of Vpr-encoding mRNA; a reduction in the rate and/or level of translation of Vpr; a reduction in the level of Vpr polypeptide; a reduction in the level of the correct folding (e.g., cotranslational folding) of Vpr polypeptide; and specific degradation of Vpr polypeptide.

The term "Vpr" as used herein, encompasses any naturally-occurring, lentiviral-encoded Vpr; variants of naturally-occurring Vpr (e.g., variants that include conservative amino acid changes compared to a naturally-occurring Vpr); synthetically or recombinantly produced Vpr; fusion proteins that include Vpr and a fusion partner, where the fusion partner is an immunological tag (e.g., an "epitope tag" such as FLAG, HA, and the like), a protein that provides a detectable signal (e.g., a fluorescent protein, such as a green fluorescent protein from Aequorea victoria; a fluorescent protein from an Anthozoa species; luciferase; β-galactosidase; and the like); radiolabeled Vpr; biotinylated Vpr; and the like. The term "Vpr" encompasses polypeptides that include Vpr and a moiety that facilitates purification and/or isolation of Vpr. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His facilitate purification of their cognate fusion proteins on immobilized glutathione, maltose, phenylarsine oxide, calmodulin, and metal-chelate resins,respectively. Variant Vpr polypeptides include variants in which one or more of $Pro^5$, $Pro^{10}$, and $Pro^{14}$ is substituted with another amino acid, e.g., Asn. In many embodiments, Vpr variants retain binding to CyPA.

The term "Vpr" further encompasses fragments of Vpr of at least about 20, at least about 50, or at least about 100 amino acids; and fusion proteins that include fragments of Vpr and a fusion partner. The term "Vpr" includes all forms of synthetic Vpr peptides and all fragments thereof chemically synthesized and/or modified by standard methods of peptide synthesis, particularly Vpr fragments that bind CyPA.

In many embodiments, Vpr fragments suitable for use include from amino acid 1 to about amino acid 50, from about amino acid 10 to about amino acid 45, from about amino acid 15 to about amino acid 40, from about amino acid 20 to about amino acid 40, or from about amino acid 1 to about amino acid 40 of Vpr. Specific, non-limiting examples of useful Vpr fragments include $Vpr^{1-40}$, $Vpr^{21-40}$, $Vpr^{30-40}$, $Vpr^{25-40}$, and the like. Typically, a Vpr fragment includes from about amino acid 30 to about amino acid 50, e.g., from about amino acid 30 to about amino acid 45, or from about amino acid 30 to about amino acid 40 of Vpr.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of lentivirus infection, the term "treatment" encompasses prevention of establishment of a systemic infection following initial contact with the virus; and prophylactic treatment of an individual not yet infected with the virus.

The terms "individual, " "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by a lentivirus that encodes Vpr.

By "genetic transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a mammalian cell, a permanent genetic change is generally achieved by introduction of the DNA into the genome of the cell.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as $CD4^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "lentivirus" as used herein, refers to human immunodeficiency virus-1 (HIV-1); human immunodeficiency virus-2 (HIV-2); simian immunodeficiency virus (SIV); and feline immunodeficiency virus (FIV).

A "therapeutically effective" amount of a subject agent is an amount that is effective to induce loss of intracellular Vpr and/or inhibition of the PPIase activity of a protein that catalyzes cis-trans isomerization of cis-peptidylprolyl bonds in Vpr in a cell when the cell is contacted with the subject agent.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an agent that induces Vpr loss" includes a plurality of such agents and reference to "the lentivirus" includes reference to one or more lentiviruses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Screening Methods

The present invention provides methods of identifying compounds that induce loss of lentiviral Vpr in a eukaryotic cell. The methods generally comprise contacting a cell that produces a lentiviral Vpr protein with a test agent, and determining the effect, if any, on the level and/or activity of Vpr protein. An agent that induces loss of Vpr in the cell is a candidate agent for treating HIV-1, HIV-2, and other lentiviral infections.

The assay can be designed in a number of ways. In some embodiments, the assay provides for determining the effect of a test agent on the level of Vpr protein in a cell. In other embodiments, the assay provides for determining the effect of a test agent on Vpr-mediated cell cycle arrest. In other embodiments, the assay provides for determining the effect of a test agent on a PPIase activity of a protein that catalyzes cis-trans isomerization of cis-peptidylprolyl bonds in Vpr. These embodiments are described in detail below.

In general, a test agent of interest is one that both induces Vpr loss and inhibits a PPIase activity of a protein that catalyzes cis-trans isomerization of cis-peptidylprolyl bonds in Vpr. A test agent that is active in one assay is typically tested in a second assay method of the invention to provide a test of its specificity. In general an agent of interest is one that both induces Vpr loss and inhibits a PPIase activity of a protein that catalyzes cis-trans isomerization of cis-peptidylprolyl bonds in Vpr, and which does not act by disrupting a Gag-cyclophilin binding interaction. In many embodiments, a test agent induces Vpr loss, inhibits a PPIase activity of a protein that catalyzes cis-trans isomerization of cis-peptidylprolyl bonds in Vpr, and reduces Vpr-induced cell cycle arrest.

The terms "candidate agent," "agent", "substance," "test agent," and "compound" are used interchangeably herein. Candidate agents encompass numerous chemical classes, and are generally synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward the cell used in the assay, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity are considered candidate agents.

Assays of the invention usually include one or more controls. Thus, a test sample includes a test agent, and a control sample has all the components of the test sample except for the test agent.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Loss of Vpr

In some embodiments, the subject screening methods involve contacting a cell that produces Vpr with a test agent, and determining the effect, if any, of the test agent on the level of intracellular Vpr, compared to the level of intracellular Vpr in the cell when not contacted with the test agent.

An agent of interest reduces a level of Vpr in a cell that produces Vpr by at least about 10%, at least about 20%, at least about 30%, at least about 40%, at least about 50%, at least about 60%, at least about 70%, at least about 80%, at least about 90%, or at least about 95% or more, compared to the level of Vpr in the cell not contacted with the test agent.

Whether a test agent induces intracellular Vpr loss can be determined by any known method for determining the level of a protein in a cell. In some embodiments, the assay is an immunological assay, using a Vpr-specific antibody. Such methods include, but are not limited to, immunoprecipitating Vpr from a cellular extract, and analyzing the immunoprecipitated Vpr by sodium dodecyl sulfate polyacrylamide gel electrophoresis (SDS-PAGE); detecting a detectable fusion partner in a cell that produces a fusion protein that includes Vpr and a fusion partner that provides a detectable signal; standard SDS-PAGE and immunoblotting (e.g., transfer of proteins from a gel generated during SDS-PAGE to a membrane, and probing the membrane with detectably labeled antibodies) of Vpr from cells producing Vpr.

In other embodiments, the assay is an assay that detects a fusion partner of a Vpr fusion protein. Thus, e.g., where the Vpr is part of a fusion protein that includes Vpr, and, as a fusion partner, a protein that provides a detectable signal, the assay detects the fusion partner. Fusion partners include, but are not limited to, a green fluorescent protein (GFP); a fluorescent protein from an Anthozoa species (see, e.g., Matz et al. (1999) Nat. Biotechnol. 17:969–973); luciferase; β-galactosidase; and the like. A construct that includes a nucleotide sequence that encodes the Vpr fusion protein is introduced into a eukaryotic cell. The level of Vpr protein that is produced in the cell is determined by detecting the fusion partner. Immunological assays (protein blots, ELISAs, etc.) are used where the fusion partner is an immunological tag. Enzymatic assays are used where the fusion partner is an enzyme (e.g., β-galactosidase, luciferase, horse radish peroxidase, etc.) that produces a detectable product. Fluorimetric assays are used to detect fusion partners that are fluorogenic. The fusion partner is detected by any known method appropriate to the fusion partner. The fusion partner is detected in a cell extract, using an assay appropriate to the fusion partner (e.g., an enzymatic assay, an immunological assay, etc.); or the fusion partner is detected in an intact cell, e.g., using flow cytometry. For example, where the fusion partner provides a fluorescent signal, the level of Vpr is determined using a flow cytometer.

In many embodiments, an assay detects a Vpr fragment. Vpr fragments suitable for use include from amino acid 1 to about amino acid 50, from about amino acid 10 to about amino acid 45, from about amino acid 15 to about amino acid 40, from about amino acid 20 to about amino acid 40, or from about amino acid 1 to about amino acid 40 of Vpr. Specific, non-limiting examples of useful Vpr fragments include $Vpr^{1-40}$, $Vpr^{21-40}$, $Vpr^{30-40}$, $Vpr^{25-40}$, and the like. Typically, a Vpr fragment includes from about amino acid 30 to about amino acid 50, e.g., from about amino acid 30 to about amino acid 45, or from about amino acid 30 to about amino acid 40 of Vpr.

In some embodiments, the assay is an assay that detects a level of correct cotranslational folding of Vpr. A level of correct cotranslational folding of Vpr can be conducted using a pulse-chase assay, as described in the Examples. Incorrect folding leads to rapid degradation of Vpr. Degradation of Vpr is detected by detecting a loss of Vpr in the cell, using assays described herein (e.g., immunological assays).

The cells used in the assay are eukaryotic cells, usually mammalian cells, including, but not limited to, primate cells, and including human cells and cell lines. The cells may be primary cell cultures or may be immortalized cell lines. Any eukaryotic cell can be used as long Vpr can be produced in the cell. Exemplary cells include human $CD4^+$ T cell lines such as Jurkat, A3.01, H9, and the like; CHO cells; 293 cells; and the like.

In many embodiments, a construct that includes a nucleotide sequence that encodes Vpr (or a fragment thereof, or a fusion protein comprising Vpr or a Vpr fragment, as described above) is introduced into the cells, such that the cells are transiently or stably genetically modified with the construct.

Cells can be genetically transformed (genetically modified) with a Vpr-encoding construct that is a viral construct; a plasmid; a YAC; and the like. Any of a variety of viral vectors can be used, including, but not limited to, adenoviral vectors, adenoassociated viral vectors, vaccinia virus vectors, retroviral vectors, baculoviral vectors, and the like. Plasmids that provide for expression in eukaryotic cells are well known in the art, and many are commercially available.

Any nucleic acid vector having a eukaryotic promoter operably linked to a nucleotide sequence encoding Vpr can be used in the invention to genetically transform a eukaryotic cell. The vectors containing the Vpr-encoding DNA sequence (or the corresponding RNA sequence) which may be used in accordance with the invention may be any eukaryotic expression vector containing the Vpr-encoding DNA or RNA sequence. For example, a plasmid can be cleaved to provide linear DNA having ligatable termini. These termini are bound to exogenous DNA having complementary, like ligatable termini to provide a biologically functional recombinant DNA molecule having an intact replicon and a desired phenotypic property.

Techniques for production of nucleic acid constructs for expression of exogenous DNA or RNA sequences (e.g., a Vpr-encoding sequence) in a host are known in the art (see, for example, Kormal et al., Proc. Natl. Acad. Sci. USA, 84:2150–2154, 1987; Sambrook et al. Molecular Cloning: A Laboratory Manual, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Various vectors (e.g., vectors capable of replication in eukaryotic hosts) can be used. Numerous vectors which can replicate in eukaryotic hosts are known in the art and are commercially available. In general, such vectors used in accordance with the invention include a eukaryotic promoter operably linked to the Vpr-encoding nucleotide sequence.

Generally, the DNA construct contains a promoter to facilitate expression of the Vpr-encoding DNA. The promoter can be a strong, eukaryotic promoter. Exemplary, non-limiting eukaryotic promoters for facilitating transcription in a eukaryotic cell include promoters from cytomegalovirus (CMV), mouse mammary tumor virus (MMTV), Rous sarcoma virus (RSV), and adenovirus early promoter. The promoter can also be an inducible promoter, e.g., a tet-inducible promoter, and the like.

For eukaryotic expression, the construct generally comprises at least a eukaryotic promoter operably linked to the Vpr-encoding sequence, which is in turn operably linked to a polyadenylation sequence. The polyadenylation signal sequence may be selected from any of a variety of polyadenylation signal sequences known in the art. Preferably, the polyadenylation signal sequence is the SV40 late polyadenylation signal sequence. The construct may also include sequences in addition to promoters which enhance expression in the cell (e.g., enhancer sequences, introns). For example, the construct can include one or more introns, which can increase levels of expression of the Vpr-encoding nucleotide sequence. Any of a variety of introns known in the art may be used.

Other components such as a marker (e.g., an antibiotic resistance gene (such as an ampicillin resistance gene) or β-galactosidase) to aid in selection of cells containing and/or expressing the construct (e.g., during the process of vector construction), an origin of replication for stable replication of the construct in a bacterial cell (e.g., a high copy number origin of replication, for propagating the vector in a bacterial cell), a nuclear localization signal; a marker that provides for selection in eukaryotic cells (e.g., hygromycin resistance, resistance to mycophenolic acid, and the like); or other elements which facilitate production of the construct, the Vpr protein encoded thereby, or both.

Methods of genetically transforming a eukaryotic cell are well known to those skilled in the art and include, but are not limited to, electroporation, lipofection, infection, use of cationic lipids, use of dextran sulfate, and the like.

Inhibition of PPIase Activity

The invention further provides methods of identifying compounds that inhibit a PPIase activity of a protein that catalyzes cis-trans isomerization of cis-peptidylprolyl bonds in Vpr. The methods generally comprise contacting a PPIase polypeptide with a test agent, and determining the effect, if any on the PPIase activity of the protein. An agent that inhibits the PPIase activity of the protein is a candidate agent for treating HIV-1, HIV-2, and other lentiviral infections.

An agent of interest inhibits the PPIase activity of a protein that catalyzes cis-trans isomerization of cis-peptidylprolyl bonds in Vpr by at least about 10%, at least about 20%, at least about 30%, at least about 40%, at least about 50%, at least about 60%, at least about 70%, at least about 80%, at least about 90%, or at least about 95% or more, compared to the PPIase activity of the protein in the absence of the test agent.

As used herein, the term "protein that catalyzes cis-trans isomerization of cis-peptidylprolyl bonds in Vpr" refers to any PPIase that catalyzes cis-trans isomerization of cis-peptidylprolyl bonds in Vpr in a eukaryotic cell. A wide variety of PPIases are known in the art and include FK506 binding proteins (FKBP), cyclophlins, and parvulins, where FKBP and cyclophilins are collectively referred to in the art as immunophilins. See, e.g., Gothel and Marahiel (1999) *Cell. Mol. Life Sci.* 55:423–436; and Shaw (2002) *EMBO Reports* 3:521–526.

As used herein, the term "cyclophilin" refers to any protein that exhibits peptidyl-prolyl cis/trans isomerase activity. Cyclophilins include, but are not limited to, cyclophilin A; cyclophilin B; cyclophilin C; and the like. Cyclophilins are known in the art, have been amply described, and any known cyclophilin, or variant thereof that has PPIase activity, can be used. See, e.g., U.S. Pat. No. 6,030,825; and Friedman et al. (1993) *Proc. Natl. Acad. Sci. USA* 90:6815–6819.

Any PPIase protein that catalyzes cis-trans isomerization of cis-peptidylprolyl bonds in Vpr can be used in the screening method of the instant invention, including a PPIase protein from any mammalian species; naturally-occurring PPIases; recombinantly or synthetically produced PPIases; and variants of naturally-occurring PPIases that retain the ability to catalyze cis-trans isomerization of cis-peptidylprolyl bonds in Vpr.

Whether a given agent inhibits the PPIase activity of a protein that catalyzes cis-trans isomerization of cis-peptidylprolyl bonds in Vpr can be determined using any known method. Assays of PPIase activity are well known in the art. See, e.g., Fisher et al. (1984) *Biochim. Biophys. Acta* 43:1101–1112. Suitable substrates include peptides of the formula Xaa-Ala-Xaa-Pro-Phe-X, where Xaa is any amino acid, and X is a moiety that provides a detectable signal. The substrate is kept under conditions in which the substrate is in equilibrium with respect to the prolyl bond, with about 80%, about 85%, about 95%, or more in the trans conformation. The substrate is acted on by the PPIase, resulting in a trans-to-cis conversion. The trans-to-cis conversion is measured by the hydrolysis of the cis conformer by chymotrypsin, which releases the X moiety, which release provides a detectable signal.

X is a tag group capable of being detected by assays that detect radiolabelled, photochemical, colorimetric, chromogenic, fluorescent, fluorogenic, phosphorescent, electrochemical, chemiluminescent or bioluminescent tags.

Tags include, but are not limited to, tags that are capable of being assayed, generally quantitatively, by radiolabels, by photochemical, colorimetric, chromogenic, fluorescent, fluorogenic, phosphorescent, electrochemical, chemiluminescent or bioluminescent or immunoassays. Exemplary tags are those detectable in colorimetric, chromogenic, fluorescent, fluorogenic, chemiluminescent or bioluminescent assays. Further exemplary tags are those that include a tag group that can be a radioactively tagged group, or a fluorogenic tag, a chromogenic tag or a chemiluminescent tag. All of these indicators form either an amide linkage or an ester linkage with the Phe such that these linkages are cleavable by the chymotrysin.

Chromogenic and fluorogenic labels and the use thereof are known in this art (see, e.g., U.S. Pat. Nos. 4,448,715; 3,884,896; 3,886,136; 4,016,042; 4,028,318; 4,119,620; 4,147,692; 4,155,916; 4,191,808; 4,191,809 4,207,232; and 4,167,449 which contain lists of specific chromogenic or fluorogenic substrates for various proteolytic enzymes; colorimetric substances are shown in U.S. Pat. Nos. 4,217,269, 4,210,497 and 4,221,706).

Fluorogenic or fluorescent tags suitable for use in the present methods include, but are not limited to, dansyl, 4-methylcoumaryl-7-amino, 4-trifluoromethylcoumaryl-7-amino, naphthylamino, 7-oxycoumaryl, 5-amino-iso-phthalic acid di(lower alkyl, preferably methyl or ethyl) ester, coumaryl-7-amino tagged with radioactive halogen or $^3$H, or naphthylamino tagged with radioactive halogen of $^3$H. Exemplary fluorogenic tags include 4-methylcoumaryl-7-amino or 4-trifluoromethylcoumaryl-7-amino. When the tag is a fluorogenic tag, it can be 4-methyl coumaryl-7-amino, 4-trifluoromethyl coumaryl-7-amino, naphthylamino, 7-oxy-coumaryl, 5-amino isophthalic acid diethyl ester, dansyl, coumaryl-7-amino, 4-trifluoromethyl coumaryl-7-amino, 2-methylanthranilic acid.

Colorimetric or chromogenic tags suitable for use in the present methods include, but are not limited to, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, naphthylamino, μ-naphthylamino, β-naphthylamino, nitronaphthylamino, 5-nitro-α-naphthylamino, methoxynaphthylamino, 4-methoxy-μ-naphthylamino, quinonylamino, quinon-5-ylamino, nitroquinonylamino, 8-nitroquinon-5-ylamino, 4-methylcoumaryl-7-amino, 4-trifluoromethylcoumaryl-7-amino, and naphthylamino tagged with radioactive halogen.

When the tag is a chromogenic tag, it can be, for example, p-nitro-anilino, p-nitro-phenyloxy, nitrophenylamino, naphthylamino, nitronaphthylamino, methoxynaphthylamino, quinolylamino, nitroquinolylamino, 4-trifluoromethyl coumaryl-7-amino, or naphthylamino.

Chemiluminescent tags suitable for use in the present methods include, but are not limited to, luminol (5-amino-2,3-dihydro-1,4-phthalazinedione), iso-luminol (6-amino-2,3-dihydro-1,4-phthalazinedione) and N-(4-aminobutyl)-N-ethyl-iso-luminol (6-(N-(4-aminobutyl)-N-ethylamino)-2,3-dihyrophthalazine-1,4-dione). See, Simpson et al. (1979) *Nature* 279:646.

Radiolabelled tags suitable for use in the present methods include, but are not limited to, either $^{14}$C- or $^{3}$H-labelled anilino, benzylamino or lower alkoxy; or a halo label, in a hydroxyanilino, naphthylamino, hydroxybenzylamino or coumaryl-7-amino group.

Alternatively, the tag can be a reporter, such as chemiluminescent tag such as, amino-isoluminol, amino-luminol or other luminol derivative; or a bioluminescent tag, such as a luciferin, particularly a coelentrazine, or a luciferase, that upon cleavage is able to react with a suitable luciferase and luciferin, respectively. Also contemplated are immunoreporters, in which a reporter-labeled antibody (or antigen, i.e., ligand) binds to an antigen (receptor) on X; and biotin/avidin linked reporters.

PPIase activity can be assayed by an enzyme assay described by Rahfeld, J. U., et al. (1994) (FEBS Lett. 352: 180–184). The assay is performed at about 10° C. in 35 mM HEPES buffer, pH 7.8. Under these assay conditions, the substrate, Succinyl-Ala-Xaa-Pro-Phe-4-p-nitroanilide, is in equilibrium with respect to the prolyl bond, with 80–95% in trans and 5–20% in cis conformation. An aliquot (2 µl) of the substrate dissolved in dimethyl sulfoxide (10 mg/ml) is added to the reaction mixture described above. The trans-to-cis conversion is measured by the hydrolysis of the cis conformer by chymotrypsin, producing 4-nitroanilide which is detected spectrophotometrically by its absorbance at 390 nm. 4-Nitroanilide appears in a time-dependent and a PPIase concentration-dependent manner. Other suitable peptides include Succinyl-Ala-Ala-Pro-Phe-p-nitroanilide.

Vpr-Mediated Cell Cycle Arrest

In some embodiments, an effect on the level of Vpr is determined by examining the effect of the test agent on Vpr-induced cell cycle arrest. Vpr induces G2 cell cycle arrest. As cells proliferate, they duplicate their DNA during the S phase from 2N to 4N. The time spent in the G2 phase of the cell cycle (where there is a 4N complement of DNA) is shorter than the time spent in G1 cycle (where there is a 2N complement of DNA). Vpr induces a delay in cell cycle progression at or near mitosis (in G2) and so cells appear to have a 4N complement of DNA for an increased time compared to normal cells. Whether a cell has a normal (2N) complement or 4N complement of DNA is readily determined by measuring the DNA content of the cell. Since the DNA content of cycling cells gives a relative time that these cells spend in each phase of the cell cycle, and the presence of intact Vpr increases the relative time spent with 4N DNA, this technique measures G2 cell cycle arrest.

Thus, in some embodiments, the invention provides a method for identifying an agent that reduces or inhibits Vpr-induced cell cycle arrest. The method generally involves contacting a cell that produces Vpr with a test agent, and determining the effect, if any, of the test agent on the DNA complement of the cell. For example, the method involves determining whether the cell has a 2N complement of DNA, or a 4N complement of DNA, i.e., determining whether the cells have a normal cell cycle profile or are paused at the G2/M checkpoint.

In some embodiments, an agent of interest inhibits Vpr-induced cell cycle arrest by at least about 10%, at least about 20%, at least about 30%, at least about 40%, at least about 50%, at least about 60%, at least about 70%, at least about 80%, at least about 90%, or at least about 95% or more, compared to the level of Vpr-induced cell cycle arrest in the absence of the test agent.

In general, determining the DNA complement of a cell is accomplished by staining the DNA. Any of a variety of agents can be used to stain DNA, including, but not limited to, propidium iodide, ethidium bromide, Hoechst dyes (e.g., Hoechst 33342, Hoechst 33258), mithramycin, DAPI (4,6-diamidino-2-phenylindole), TO-PRO-3, chromomycin, and acridine orange. In general, any dye that binds DNA and can be detected using, e.g., flow cytometric methods, is suitable.

Any eukaryotic cell can be used, as long as it is a dividing cell. Suitable eukaryotic cells include those described above. Vpr, and constructs that include a nucleotide sequence that encodes Vpr, are described above. A construct that includes a nucleotide sequence that encodes Vpr is introduced into the cell, as described above.

In some embodiments, cells are fixed before being contacted with the DNA-binding dye. For example, cells may be fixed by treating with 4% paraformaldehyde for from about 30 minutes to about one hour, usually at about 4° C. Cells may also be fixed by treating with 50%–75% ethanol for from about 30 minutes to about one hour, usually at about 4° C.

Exemplary, non-limiting protocols for staining cells in preparation for flow cytometry include the following:

1) Propidium iodide (PI) staining Cells are suspended in a buffer (e.g., phosphate buffered saline (PBS) containing 2% fetal bovine serum (FBS); PBS containing 0.1% bovine serum albumin (BSA); or similar buffer), then washed and resuspended at 1–2×10$^{6}$ cells/ml in the same buffer. The cell suspension is aliquoted into tubes at 1 ml/tube and 3 ml cold absolute ethanol is added while mixing, to fix the cells. The cells are fixed for one hour at 4° C. Cells may be stored in 70% ethanol at −20° C. for several weeks prior to PI staining and flow cytometric analysis. After fixing, the cells are washed two times in PBS, then pelleted by centrifugation. One ml of a PI staining solution (3.8 mM sodium citrate, 50 µg/ml PI in PBS) is added to the cell pellet and the cell pellet is resuspended in the PI staining solution. If desired, 50 µl of an RNAse A stock solution (10 µg/ml RNAse A) is added. The samples are kept at 4° C. until being analyzed by flow cytometry.

2) Hoechst staining. Cells are washed in a buffer (e.g., phosphate buffered saline (PBS) containing 2% fetal bovine serum (FBS); PBS containing 0.1% bovine serum albumin (BSA); or similar buffer), then washed and resuspended at 1×10$^{6}$ cells/ml in the same buffer. An equal volume of Hoechst dye (working solution 5 mM) is added, and the cells are kept for 15 minutes at 37° C. After staining, the cells can be directly analyzed for fluorescence, or washed and fixed in paraformaldehyde (1% in PBS) for future analysis.

Once the DNA is detectably labeled, the cells are analyzed by flow cytometry. Flow cytometric methods are amenable to high through-put screening formats. Any of a number of instruments can be used to analyze the cells. Non-limiting examples of such instruments are Coulter® Epics XL (Beckman Coulter); DAKO Galaxy™ Flow Cytometry System (DAKO); FACStar+™ (Becton-Dickinson); FACSCalibur (Becton-Dickinson); or any similar instrument.

As noted above, an agent of interest is one that does not act by disrupting Gag-cyclophilin binding. Whether a test agent inhibits Gag-cyclophilin binding can be determined using any known method. See, e.g., U.S. Pat. No. 5,840,305; and 5,773,225. Generally, the test agent is contacted in a test sample with a cyclophilin and a Gag protein, and the effect, if any, of the test agent on cyclophilin-Gag binding is determined, e.g., by measuring the amount of cyclophilin-Gag complexes in the presence and in the absence of the test agent. Measuring the amount of cyclophilin-Gag complexes can be achieved, e.g., by using an immunologically tagged cyclophilin and/or an immunologically tagged Gag protein, and immunoprecipitating the complexes with antibody specific for the immunological tag.

Agents that Induce Loss of Lentiviral Vpr

The present invention further provides agents that induce loss of lentiviral Vpr, and agents that inhibit a PPIase activity of a protein that catalyzes cis-trans isomerization of cis-peptidylprolyl bonds in Vpr. Of particular interest in many embodiments are agents identified using a screening method of the invention. The subject agents are useful for inhibiting lentiviral replication, and are therefore useful for treating lentiviral infections.

Formulations

In general, a subject agent is prepared in a pharmaceutically acceptable composition for delivery to a host.

Pharmaceutically acceptable carriers preferred for use with a subject agent may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a subject agent may also be lyophilized using means well known in the art, for subsequent reconstitution and use according to the invention.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like. In one embodiment, a subject agent formulation comprises additional anti-mycobacterial and/or anti-bacterial agent(s).

A subject agent can be administered in the absence of agents or compounds that might facilitate uptake by target cells. A subject agent can be administered with compounds that facilitate uptake of a subject agent by target cells (e.g., by macrophages) or otherwise enhance transport of a subject agent to a treatment site for action. Absorption promoters, detergents and chemical irritants (e.g., keratinolytic agents) can enhance transmission of a subject agent into a target tissue (e.g., through the skin). For general principles regarding absorption promoters and detergents which have been used with success in mucosal delivery of organic and peptide-based drugs, see, e.g., Chien, *Novel Drug Delivery Systems*, Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Tables 3–4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the subject agent to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2–4.0 Fm can encapsulate a substantial percentage of an aqueous buffer comprising large macromolecules. RNA and DNA can be encapsulated within the aqueous interior and be delivered to cells in a biologically active form (Fraley, et al., (1981) *Trends Biochem. Sci.*, 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.*, 19:189; Grabarek, et al., (1990) *Anal. Biochem.*, 185:131; Staros, et al., (1986) *Anal. Biochem.* 156:220 and Boujrad, et al., (1993) *Proc. Natl. Acad. Sci. USA*, 90:5728). Targeted delivery of a subject agent can also be achieved by conjugation of a subject agent to a the surface of viral and non-viral recombinant expression vectors, to an antigen or other ligand, to a monoclonal antibody or to any molecule which has the desired binding specificity.

Method of Treating a Lentivirus Infection

The present invention provides methods of treating a lentivirus infection in an individual. The methods generally involve administering to an individual having a lentivirus infection a subject agent in an amount effective to induce loss of Vpr in a lentivirus-infected cell in the individual, thereby treating the lentivirus infection.

A therapeutically effective amount of an agent that induces Vpr loss in a lentivirus-infected cell is an amount that reduces a level of Vpr in the lentivirus-infected cell and/or reduces lentivirus load in the individual and/or reduces lentivirus replication in a lentivirus-infected cell in the individual by at least about 10%, at least about 20%, at least about 30%, at least about 40%, at least about 50%, at least about 60%, at least about 70%, at least about 80%, at least about 90%, or at least about 95% or more, compared to the levels of Vpr or lentivirus load or lentivirus replication in a lentivirus-infected cell of the individual not treated with the agent.

Treating a lentivirus infection, includes, but is not limited to, preventing lentivirus infection, reducing the probability of lentivirus infection, reducing the spread of lentivirus from an infected cell to a susceptible cell, reducing viral load in an lentivirus-infected individual, reducing an amount of virally-encoded polypeptide(s) in an lentivirus-infected individual, and increasing CD4 T cell count in an lentivirus-infected individual.

The amount of subject agent which is administered will vary with the nature of the drug. As one non-limiting example, a subject agent can be administered in the range of about 0.2 to 20 mg/kg/day. The determination of how large a dosage to be used may be determined using the small animal model and relating the dosage based on pharmacokinetics, e.g. with equations predictive of interspecies scaling. Usually, the lowest effective dose will be used.

Routes of Administration

A subject agent is administered to an individual using any available method and route suitable for drug delivery.

Conventional and pharmaceutically acceptable routes of administration include intranasal, intramuscular, intratracheal, intratumoral, subcutaneous, intradermal, topical application, intravenous, vaginal, rectal, nasal, oral and other parenteral routes of administration. Routes of administration may be combined, if desired, or adjusted depending upon the subject agent and/or the desired effect on the immune response. The subject agent can be administered in a single dose or in multiple doses, and may encompass administration of booster doses, to maintain the desired effect.

A subject agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Inhalational routes of administration (e.g., intranasal, intrapulmonary, and the like) are particularly useful in stimulating an immune response for prevention or treatment of infections of the respiratory tract. Such means include inhalation of aerosol suspensions or insufflation of the polynucleotide compositions of the invention. Nebulizer devices, metered dose inhalers, and the like suitable for delivery of polynucleotide compositions to the nasal mucosa, trachea and bronchioli are well-known in the art and will therefore not be described in detail here. For general review in regard to intranasal drug delivery, see, e.g., Chien, *Novel Drug Delivery Systems*, Ch. 5 (Marcel Dekker, 1992).

Parenteral routes of administration other than inhalation administration include, but are not necessarily limited to, topical, transdermal, subcutaneous, intramuscular, intraorbital, intraspinal, intrasternal, and intravenous routes, i.e., any route of administration other than through the alimentary canal. Parenteral administration can be carried to effect systemic or local delivery of subject agent.

Systemic administration typically involves intravenous, intradermal, subcutaneous, or intramuscular administration or systemically absorbed topical or mucosal administration of pharmaceutical preparations. Mucosal administration includes administration to the respiratory tissue, e.g., by inhalation, nasal drops, ocular drop, etc.; anal or vaginal routes of administration, e.g., by suppositories; and the like. A subject agent can also be delivered to the subject by enteral administration. Enteral routes of administration include, but are not necessarily limited to, oral and rectal (e.g., using a suppository) delivery.

Any of a variety of methods can be used to determine whether a treatment method is effective. For example, methods of determining whether the methods of the invention are effective in reducing lentivirus entry into a cell, and/or treating an lentivirus infection, are any known test for indicia of lentivirus infection, including, but not limited to, measuring viral load, e.g., by measuring the amount of lentivirus in a biological sample, e.g., using a polymerase chain reaction (PCR) with primers specific for a lentivirus polynucleotide sequence; detecting and/or measuring a polypeptide encoded by lentivirus, e.g., p24, gp120, reverse transcriptase, using, e.g., an immunological assay with an antibody specific for the polypeptide; and measuring CD4 cell count in the individual. Methods of assaying an lentivirus infection (or any indicia associated with an lentivirus infection) are known in the art, and have been described in numerous publications such as *HIV Protocols* (*Methods in Molecular Medicine*, 17) N. L. Michael and J. H. Kim, eds. (1999) Humana Press.

Combination Therapies

A subject agent can be administered to an individual in combination (e.g., in the same formulation or in separate formulations) with another therapeutic agent ("combination therapy"). The subject agent can be administered in admixture with another therapeutic agent or can be administered in a separate formulation. When administered in separate formulations, a subject agent and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more. Effective amounts of a therapeutic agent are as described above.

Therapeutic agents that can be administered in combination therapy, such as anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, patients with a viral or bacterial infection are treated with a combination of one or more subject agents with one or more of the following: beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonofonnate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof. Anti-HIV agents are those in the preceding list that specifically target a function of one or more HIV proteins.

Subjects Suitable for Treatment

The methods of the present invention are suitable for treating individuals who have a lentiviral infection; who are at risk of contracting a lentiviral infection; and who were treated for a lentiviral infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers. Individuals suitable for treatment include individuals infected with, or at risk of becoming infected with, HIV-1 and/or HIV-2 and/or HIV-3, or any variant thereof.

Individuals suitable for treatment with the methods of the invention also include individuals who have a lentiviral infection that is refractory to treatment with other antiviral therapies.

Individuals suitable for treatment include non infected individuals that have a high risk of lentivirus exposure and should be protected from establishment of lentivirus infection following exposure to lentivirus.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Studies on Vpr-CyPA Interaction Using BIAcore Spectroscopy: the Binding of the Vpr N-Terminus Requires Pro-35.

Surface plasmon resonance biosensor analysis (BIAcore-Spectroscopy) was applied to analyze the molecular aspects that govern interaction of Vpr with CyPA. For the first experiment, a novel peptide comprising the first 40 residues of the Vpr protein derived from the isolate HIV-1$_{NL4-3}$ was used to study the interaction with CyPA.

Surface plasmon resonance measurements were performed at 25° C. using a BIACORE 2000 (BIAcore AB, Upsala Sweden) equipped with a CM5 research-grade sensor chip. Recombinant CyPA (Sigma) was immobilized at a concentration ranging from 4200 to 11200 response units (RUs) on flow cells 2, 3 and 4 using standard amine-coupling chemistry (NHS/EDC, Johnson et al., 1991) while flow cell 1 was used as reference cell that did not carry CyPA. The peptide Vpr$^{1-40}$ was dissolved at concentrations ranging from 1 to 250 µM in a running buffer (10 mM Hepes, 150 mM NaCl, 50 µM EDTA, 0.005% Tween 20, pH 7.4) and was injected over the flow cells containing CyPA bound to the chip matrix at a flow rate of 5 µl/min. Data were collected at a rate of 2.5 Hz during the 120 s association and dissociation phase. Vpr$^{1-40}$ interactions reached equilibrium rapidly and dissociation completely within 30 seconds. Results were corrected by the RU-values of the reference cell (without CyPA) to exclude unspecific binding of Vpr to the chip matrix. The experiment was repeated at least three times with two different charges of peptide and CyPA and reproducible results were obtained. The results are shown in FIGS. 1A–F.

Synthetic Vpr$^{1-40}$ and mutants carrying Pro to Asn exchanges at either amino acid positions 5, 10 and 14 (P$^{5,10,14}$ to N ) or at position 35 (P$^{35}$ to N) or at all four positions (P$^{5,10,14,35}$ to N) were purified to homogeneity, and tested for binding to immobilized recombinant CyPA using the same surface plasmon resonance biosensor system. While wild type Vpr$^{1-40}$ exhibited a concentration dependent binding to CyPA, mutation of Pro-35 to Asn completely abrogated Vpr binding. Surprisingly, mutation of prolines at positions 5, 10, and 14 (P$^{5,10,14}$ to N) retained dose-dependent binding to CyPA. Thus, among prolines at positions 5, 10, 14, and 35 of Vpr$^{1-40}$, only proline-35 is essential for binding to CyPA.

We also found that the very N-terminal fragment Vpr$^{1-20}$ did not bind to CyPA and mutation of Pro-residues in positions 5, 10, and 14 of Vpr$^{1-20}$ did not support any interaction with CyPA. We also found that the very C-terminus, exemplified as the peptide Vpr$^{47-96}$, did not interact with CyPA.

In contrast, examination of the smaller fragment, Vpr$^{21-40}$, revealed strong and dose-dependent binding to CyPA with an affinity similar to that observed for Vpr$^{1-40}$. As before for Vpr$^{1-40}$, mutating Pro-35 to Asn of Vpr$^{21-40}$ resulted in a complete loss of CyPA binding.

As a result of those BIAcore studies, it can be concluded that the novel interaction between CyPA and Vpr requires the N-terminal half of Vpr with an essential function provided by Pro-35.

Example 2

Demonstration of Vpr-CyPA Interaction by Far-Western Blotting

In order to demonstrate binding of Vpr to CyPA in context of full length Vpr the Far-Western Blot technique was applied. Investigation of full length Vpr$^{1-96}$ was not possible by BIAcore as the full length Vpr protein tends to undergo self association and protein precipitation, that all together yielded false positive binding signals. As an alternative we investigated the binding of Vpr to CyPA bound to nitrocellulose. The overlay, or Far-Western Blot method, clearly demonstrated for the first time a direct and specific binding of Vpr to CyPA.

For the purpose of Far-Western Blot technique, purified recombinant CyPA was separated in a 15% SDS PAGE at a concentration of ~150 ng CyPA per lane. Proteins were electro transferred onto nitrocellulose and individual strips of this CyPA-containing Western blot were blocked for 4 hours with 3% BSA in TBS. Strips were then incubated for 12 hrs at 4° C. with the peptide Vpr$^{1-96}$ at a concentration of 1 µg/ml, CyPA strips were incubated either in the absence of any detergent, or under more stringent conditions in TBS/T containing 0.5% Triton X100™ non-ionic detergent. Finally, strips were washed tree times in TBS/T for 10 minutes and bound Vpr was identified with anti-Vpr$^{1-96}$ (polyclonal antibodies raised in rabbits) followed by anti-rabbit IgG horse radish peroxidase (HRP) conjugate and enhanced chemiluminescence (ECL) staining. As a control, the CypA binding protein, HIV-1 capsid p24 was tested in parallel.

A band was seen at the position expected for CyPA in the absence of detergent, indicating that Vpr binds to CyPA in the absence of detergent. The degree of binding was reduced in the presence of 0.5% TritonX100™ non-ionic detergent. These studies clearly demonstrate for the first time specific interaction between Vpr and CyPA. BIAcore spectroscopy analysis performed with Vpr peptides indicated that the interaction between Vpr peptides and CyPA is a high affinity interaction. Far Western binding studies between CyPA and full-length Vpr carried out in the presence of detergents indicate that the Vpr/CyPA interaction is low affinity.

Example 3

Expression of Vpr is Reduced in HIV-1 Infected CyPA−/− Knock Out Cells

Human $CD4^+$ T cells (Jurkat), either wild type or the knock out line CyPA−/− (Braaten and Luban, 2001), were infected with equal infectious doses of HIV-$1_{NL4-3}$ expressing wild type Vpr. In the knock out cell line CyPA−/− both cypa alleles were genetically inactivated by homologous recombination and thus this CyPA−/− cell line does not express any molecules of CyPA. At peak virus replication (day 7 post infection) a pulse/chase experiment was conducted in both cultures. Cells were metabolically labeled with $[^{35}S]$-methionine for 5 minutes and chased in the absence of radioactively labeled methionine for up to 8 hrs. Cell lysates were prepared in detergents buffer and Gag as well as Vpr proteins were immunoprecipitated using anti-p24$^{CA}$ and anti-Vpr antibodies. The results indicate that there was significantly less Vpr (compared to the level of p24$^{CA}$) recovered from CyPA−/− knock out cells when compared to wild type cells. In summary, these results support our finding that CyPA is necessary for optimal expressing, folding, and stability of Vpr in HIV-1 infected cells.

Example 4

CsA Reduces the Level of Vpr in Cytosol and Nucleus in a Dose-Dependent Manner

HeLa cells were transfected with Vpr expression vector pCMV-Vpr-Fl expressing Vpr derived from the HIV-$1_{NL4-3}$ isolate: The Vpr sequence is tagged C-terminal by the FLAG epitope for purpose of efficient immune precipitation. Cells were treated with 5, 10, 25, and 50 μg/mg of CsPA starting 60 minutes prior to pulse labeling. HeLa cells were pulse-labeled for 5 minutes and chased for up to 30 minutes. Cells were lysed in isotonic buffer and fractionated into nucleus and cytosol fraction by differential centrifugation. Vpr proteins were immunoprecipitated by using anti Flag monoclonal antibodies and separated in a 10–16% SDS PAGE. Relative amounts of Vpr were quantified by image analysis, and plotted against time. The results are shown in FIGS. 2A, 2B, 3A, and 3B.

Figure 2A:
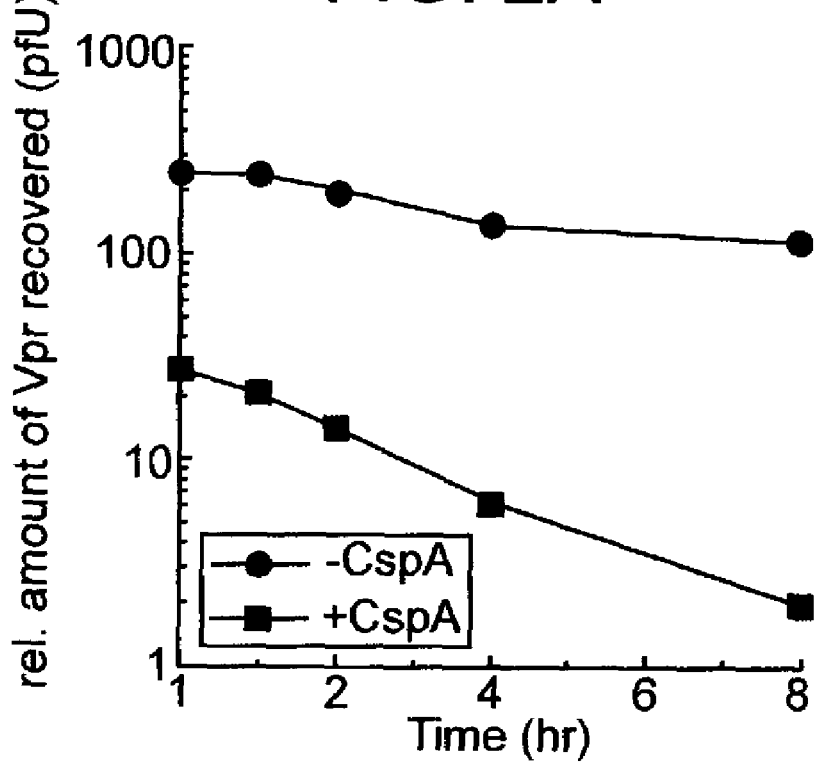
FIGS. 2A and 2B depict results demonstrating that the CyPA inhibitor CsA induces rapid loss of Vpr in HIV-1 expressing HeLa cells.
Figure 2B:
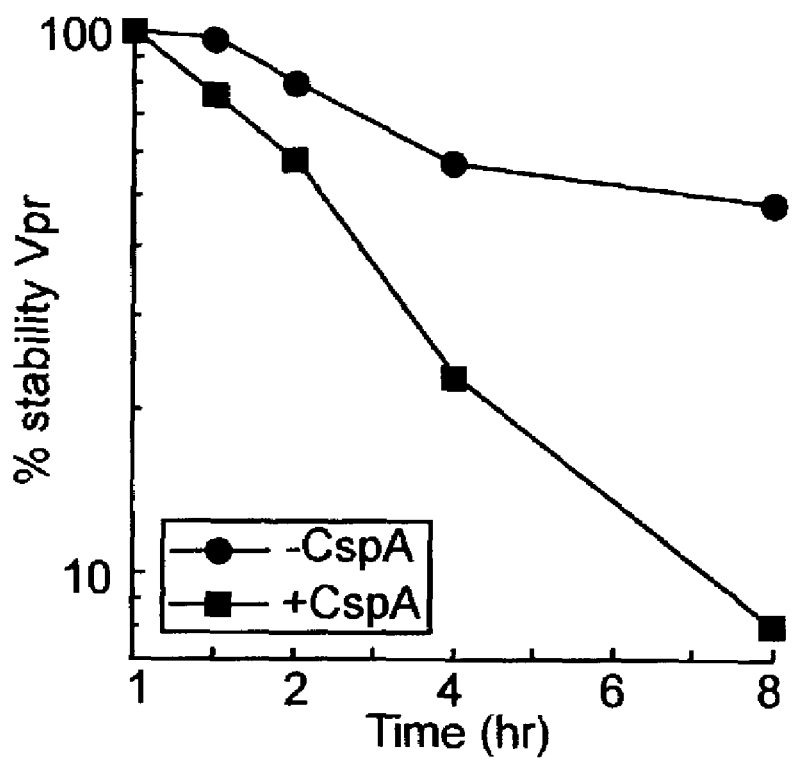

CsA caused a reduction in the relative amount and the stability of Vpr (FIGS. 2A and 2B). Parallel cultures of transfected HeLa cells were treated or not treated with 50 μg/ml CsP starting 30 minutes prior to a 15-minute pulse with $^{35}$S-methionine, and treatment was continued throughout the experiment. Vpr was immunoprecipitated with polyclonal anti-Vpr antibodies and detected in SDS-PAGE by fluorography. A very strong drop in Vpr levels recovered in the presence of CsA was observed. This effect was not due to non-specific inhibition of expression of HIV proteins, since Gag polyprotein expression and processing was not affected by CsA. HeLa cells were transfected with the CMV-driven expression vector pVprFlag, that directs the synthesis of Vpr that is C-terminally tagged with a 12-amino acid FLAG epitope. Vpr was recovered with M2-specific antibodies, separated by SDS-PAGE, and analyzed by fluorography. Both the relative amount and the stability of Vpr were estimated by image analyses and plotted against time. There was a 10-fold reduction in Vpr levels right at the end of the pulse labeling period that extended to an additional 10-fold difference at the end of the 8 hour chase period. This additional loss indicates a decrease in stability of Vpr during CsA treatment. Thus, a dramatic, nearly 100-fold reduction of Vpr levels in the presence of CsA was observed.

CsA caused a rapid reduction in the level of Vpr in both the cytosol and in the nucleus (FIGS. 3A and 3B). We conducted short term pulse chase experiments. Treatment with increasing doses of CspA started 30 min prior to a 5 min pulse, and was continued throughout a 30 min chase. As before, a dose dependent reduction in the amount of Vpr was observed that started with approximately 3-fold reduction in the presence of 10 μg/ml of CspA and was >10-fold in the presence of 50 μg/ml of CspA. However, even under these short term kinetics rapid loss of Vpr was eminent right at the beginning of the chase. A similar effect was also observed when Vpr was recovered from the nuclear fraction demonstrating that the shuttling of Vpr in and out the nucleus was not affected Further experiments demonstrated that proteosome inhibitors do not restore Vpr stability after treatment with CsA. In the nucleus fraction one can see a slight increase during the first 5 minutes of the chase independently of CyPA inhibition. This could be consequent to the transport of newly synthesized Vpr into the nucleus. In other words, what ever happens after synthesis of Vpr is not affect by CspA; Vpr continues to shuttle with the same efficiency in and out the nucleus.

When pulse chase experiments were conducted with and without proteosome inhibitors the CspA-mediated deficiency in Vpr expression was still observed. In addition, no evidence for accumulation of poly-Ubiquinated Vpr was observed following proteosome inhibition. Proteasomes are present in the cytosol and nucleus and Vpr expression was unaffected by proteosome inhibitor in CspA treated cells in both the cytosol and nuclear fraction. Thus, proteasome pathway is not involved.

Example 5

Structural Analyses of Vpr

Various structural analyses of Vpr were conducted. A cis/trans phenomenon was identified in residues Pro-5, Pro-10, Pro-14, and Pro-35 of Vpr by $^1$H NMR experiments on the peptide Vpr$^{1-40}$, the proline residues in Vpr flanking a very stable alpha helix extending from Pro-14 to Pro-35. The high resolution structure of Vpr$^{1-40}$ was determined by NMR spectroscopy and Molecular Dynamic Structure calculation. The secondary structure of Vpr was analyzed by CD spectroscopy.

Figure 4:
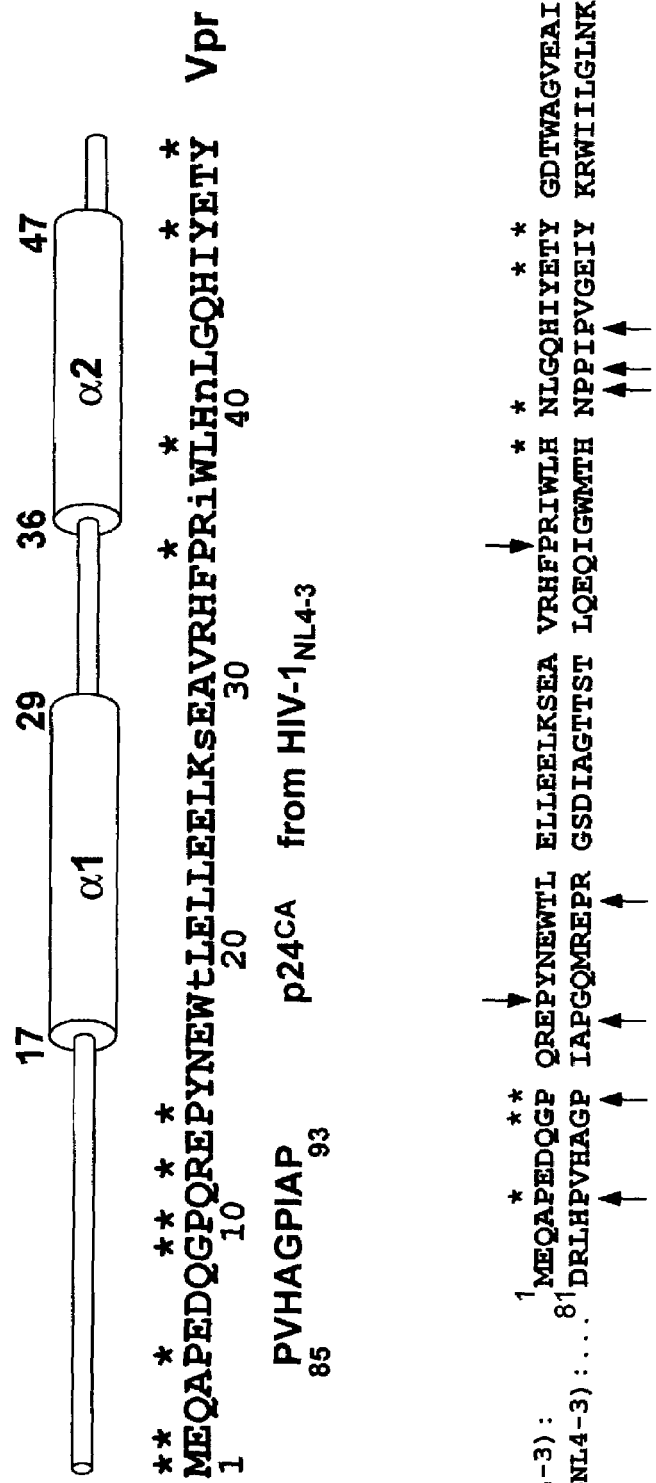
FIG. 4 provides an amino acid sequence alignment of Vpr and p24 (CA), and localization of potential CyPA binding sites and conserved Pro residues.

Conservation of a CyPA binding motive with the Vpr N-terminus is shown in FIG. 4. Amino acid sequence alignment of Vpr isolates derived from HIV-1 isolates are demonstrated and compared to that of the isolated HIV-$1_{NL4-3}$ used for peptide synthesis and infection/transfection experiments. Conserved residues are marked in bold font. Demonstration of conserved Proline residues in positions Pro-4, Pro-10, Pro-14 and Pro-35 comprising a typical CyPA binding motif. Secondary structural elements are indicated for the N-terminal region of Vpr.

Example 6

Effect of CsA on Vpr-Induced Cell Cycle Arrest

Assessment of DNA Content by Flow Cytometry

Cell-cycle analysis for HA-Vpr constructs was performed by cotransfecting pEGFP (Enhanced Green Fluorescent Protein) (Clontech) and HA-Vpr DNA constructs into 293T cells in a 1:8 molar ratio to identify plasmid-expressing cells. 36 hours later cells were trypsinized, fixed in 2% formaldehyde for 30 minutes, washed, and treated with 0.1 mg/ml Ribonuclease (RNase) A (Sigma) and 10 mg/ml propidium iodide in PBS for 30 minutes. Cellular DNA content in the transfected (GFP$^+$) and untransfected (GFP$^-$) cells was assessed using a FACScan flow cytometer.

Figure 5:
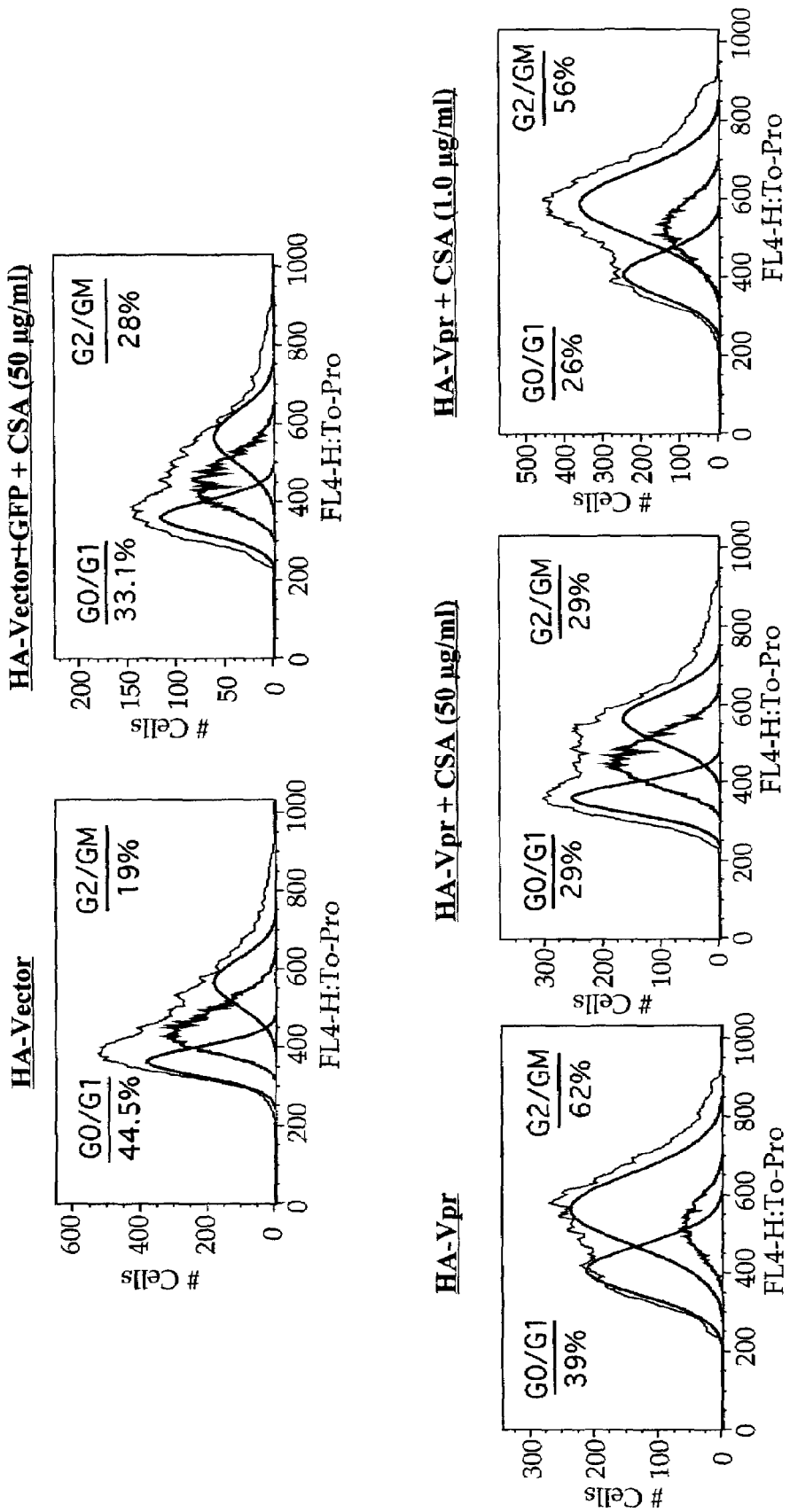
FIG. 5 depicts FACS plots showing the effect of CsA on Vpr-induced G2 cell cycle arrest.

Cells transfected with HA-vector, HA-vector +GFP or HA-Vpr were treated with CsA, and the effect of Vpr-induced cell cycle arrest was analyzed. The results are shown in FIG. 5.

Parental Jurkat cells and Jurkat CyPA knock out cells were infected with HIV-1$_{NL4-3}$ and the amount of Vpr in virions produced from the cells was analyzed by immunoblotting. Vpr was not detected in virions produced by CyPA knockout cells infected with HIV-1$_{NL4-3}$; as a control, we observed that levels of p24 were unaffected.

Figure 6:
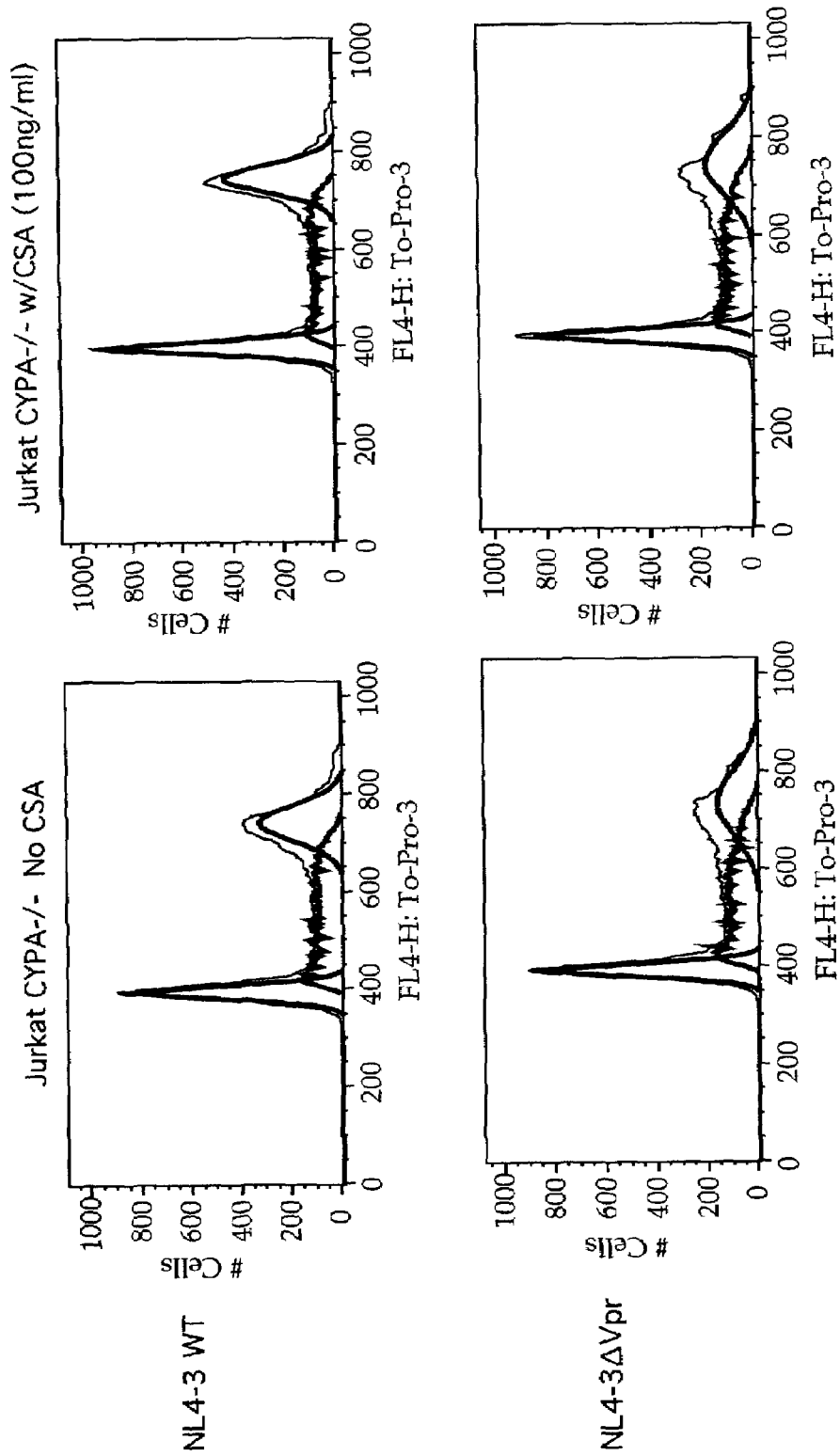
FIG. 6 depicts FACS plots showing that CyPA knockout cells are resistant to Vpr-induced G2 cell cycle arrest.

The effect of CsA on Vpr-induced cell cycle arrest was analyzed in Jurkat CyPA knockout cells. The results are shown in FIG. 6. The results indicated that CyPA knockout cells are resistant to Vpr-induced G2 cell cycle arrest.

Both Jurkat CyPA knockout cells and CsA-treated parental Jurkat cells infected with HIV produce virions that have a reduced amount of Vpr per virion. Such virions are known to be less infectious.

Example 7

CyPA Forms a Disulfide-Linked Complex with Vpr In Vitro

To investigate the nature of the complexed formed between CyPA and Vpr, 1 μg of recombinant CyPA and Vpr$^{1-96}$ were incubated in buffer at 22° C. for 12 hours, and aliquots were then denatured in sodium dodecyl sulfate-polyacrylamide gel electrophoresis (SDS-PAGE) sample buffer without reducing agents. Proteins were separated on a 14% polyacrylamide gel in SDS (without reducing agents), by PAGE. Proteins were detected by Western blotting after transfer of the proteins from the gel to membranes. CyPA and Vpr proteins were detected using anti-Vpr and anti-CyPA antibodies (Calbiochem).

Several high molecular weight complexes of CyPA were detected, in addition to the 18 kDa molecule, which may represent intermolecular homo oligomeric complexes of CyPA. In addition, incubation of CyPA with Vpr$^{1-96}$ resulted in formation of a novel approximately 29 kDa product that was stained with both anti-Vpr and anti-CyPA antibodies. Addition of a reducing agent (β-mercaptoethanol) resulted in loss of the Vpr/CyPA complex. The observation of this CyPA/Vpr complex in the absence of reducing agent, but not in the presence of reducing agent, indicates formation of a disulfide linkage between Vpr and CyPA.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of identifying a candidate agent for treating a lentivirus infection in a cell the method comprising:
   a) contacting a cell that produces a Vpr protein with a test agent; and
   b) determining the effect, if any, of the test agent on a peptidyl-prolyl cis/trans isomerase (PPIase) activity of a PPIase protein that catalyzes cis-trans isomerization of cis-peptidylprolyl bonds in Vpr, wherein an agent that inhibits PPIase activity of the PPIase protein reduces the level of Vpr in the cell, and wherein a test agent that reduces the level of Vpr in the cell is a candidate agent for treating a lentivirus infection in the cell.

2. The method of claim 1, wherein said determining comprises detecting PPIase activity using as a substrate a compound of the formula Xaa-Ala-Xaa-Pro-Phe-X, where Xaa is any amino acid, and wherein X is a moiety that provides a detectable signal.

3. The method of claim 1, wherein the compound is Succinyl-Ala-Ala-Pro-Phe-p-nitroanilide.

4. The method of claim 1, further comprising determining the effect, if any, of the agent on Vpr-induced cell cycle arrest.

5. The method of claim 4, wherein said determining step comprises determining the DNA complement of the cell.

6. The method of claim 5, wherein said determining step comprises staining the cell with a DNA binding dye.

7. The method of claim 6, wherein the DNA binding dye is propidium iodide.

8. The method of claim 1, wherein the PPIase protein is a cyclophilin.

9. The method of claim 2, wherein X is selected from a chromogenic label, a fluorogenic label, a chemiluminescent label, and a radiolabels.

* * * * *

UNITED STATES PATENT AND TRADEMARK OFFICE
CERTIFICATE OF CORRECTION

PATENT NO. : 7,108,988 B2 Page 1 of 1
APPLICATION NO. : 10/285263
DATED : September 19, 2006
INVENTOR(S) : Michael Sherman It is certified that error appears in the above-identified patent and that said Letters Patent is hereby corrected as shown below:

Column 1, line 12, insert the following statement:

--STATEMENT REGARDING FEDERALLY SPONSORED RESEARCH

This invention was made with government support under grant no. AI001866 awarded by the National Institutes of Health. The government has certain rights in this invention.--

Signed and Sealed this

Twenty-seventh Day of July, 2010

David J. Kappos
*Director of the United States Patent and Trademark Office*